United States Patent [19]

O'Brien et al.

[11] Patent Number: 5,080,478
[45] Date of Patent: Jan. 14, 1992

[54] APPARATUS FOR TESTING DARK ADAPTATION

[75] Inventors: David M. O'Brien, Raheny; Thomas P. Grennan, Terenure; Peter A. Davison, Bray, all of Ireland

[73] Assignee: Optometrics Limited, Dublin, Ireland

[21] Appl. No.: 409,203

[22] Filed: Sep. 19, 1989

[30] Foreign Application Priority Data

Sep. 21, 1988 [IE] Ireland .................. 2222/88

[51] Int. Cl.⁵ .................................. A61B 3/02
[52] U.S. Cl. ........................... 351/224; 351/243; 351/246
[58] Field of Search ............. 351/224, 225, 226, 239, 351/243, 246

[56] References Cited

U.S. PATENT DOCUMENTS

| | | | |
|---|---|---|---|
| 2,239,164 | 4/1941 | Wigelsworth | 351/243 |
| 3,883,234 | 5/1975 | Lynn et al. | |
| 3,936,162 | 2/1976 | Krakav et al. | 351/246 |
| 4,545,658 | 10/1985 | Weiss | 351/243 |
| 4,558,933 | 12/1985 | Murr | 351/226 |
| 4,634,243 | 1/1987 | Massof et al. | 351/224 |
| 4,824,237 | 4/1989 | Ratner et al. | 351/224 |

FOREIGN PATENT DOCUMENTS

| | | |
|---|---|---|
| 3135384 | 10/1983 | Fed. Rep. of Germany . |
| 2215923 | 8/1974 | France . |
| 2114406 | 8/1983 | United Kingdom . |

Primary Examiner—Rodney B. Bovernick
Assistant Examiner—J. P. Ryan
Attorney, Agent, or Firm—Sughrue, Mion, Zinn Macpeak & Seas

[57] ABSTRACT

Apparatus for testing dark adaptation comprises a test panel. Four test stimuli, comprising arrays of light emitting diodes, are arranged on the test panel around a fixation light emitting diode. Translucent covers are mounted over the arrays of light emitting diodes. Four switches to enable a subject to input the identity of a visible test stimulus are provided, each switch is operated by a button formed by a respective cover of the test stimuli. A test stimulus is randomly selected and switched on at a predetermined level of luminance. On a correct identification, another test stimulus is selected and switched on at a reduced level of luminance. The times from the commencement of the test until the various correct identifications are recorded, as are the corresponding level of luminance of the test stimuli.

20 Claims, 7 Drawing Sheets

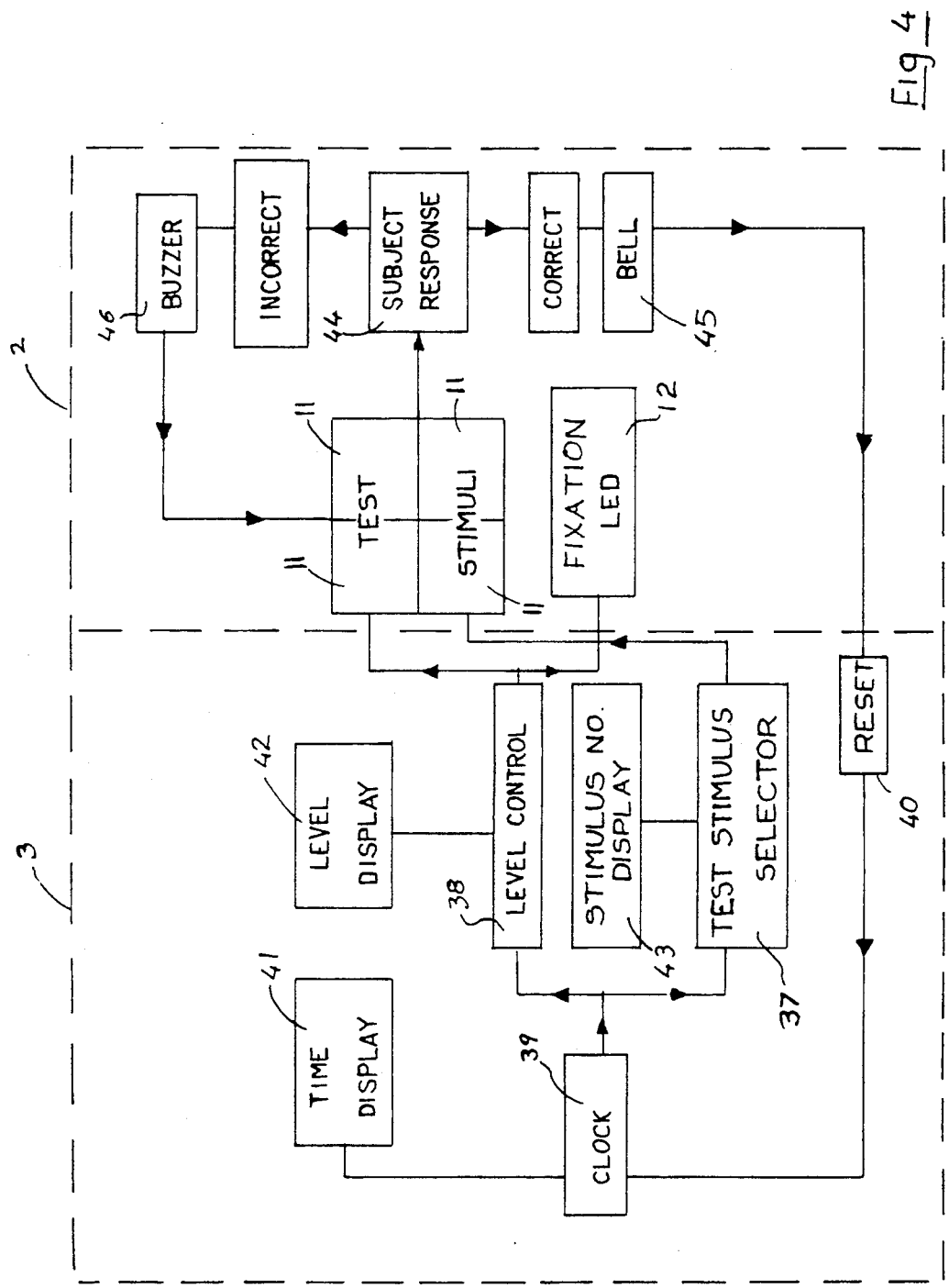

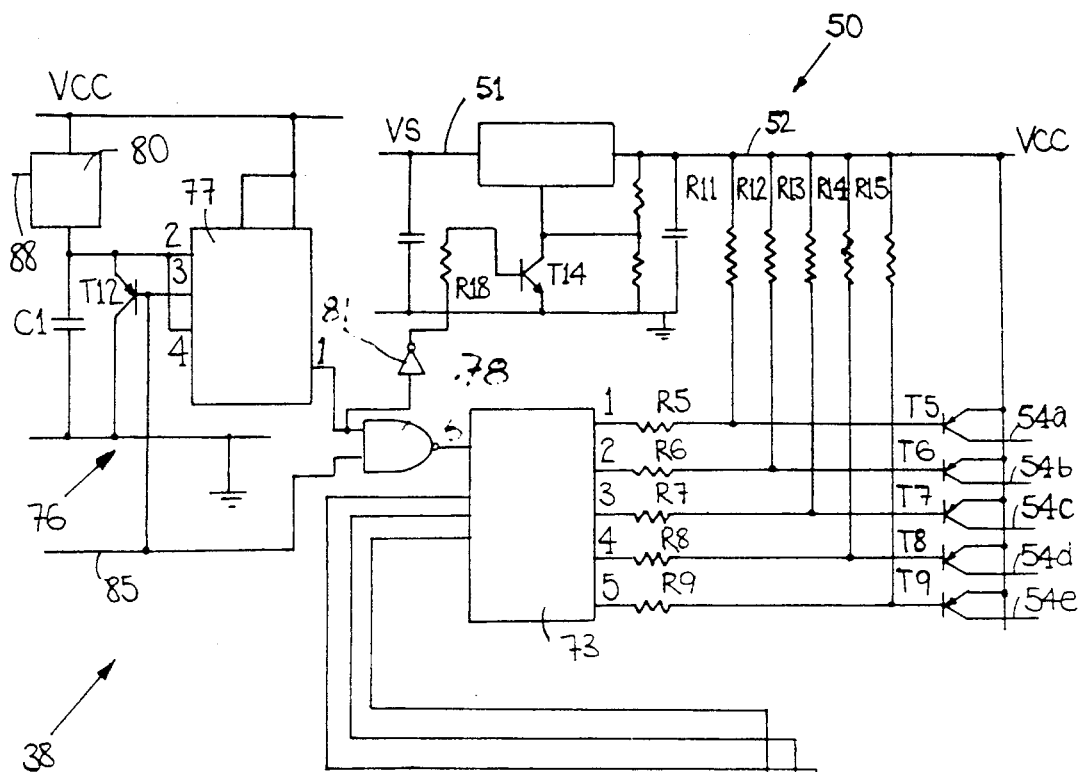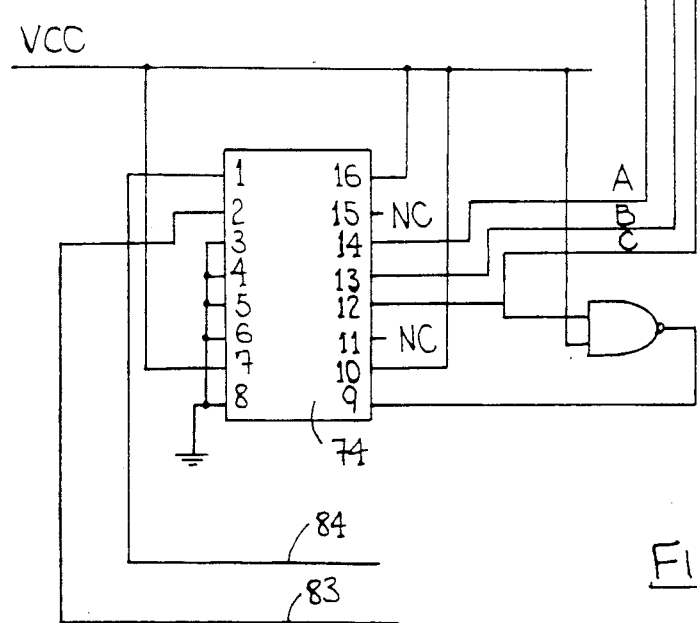
FIG 6

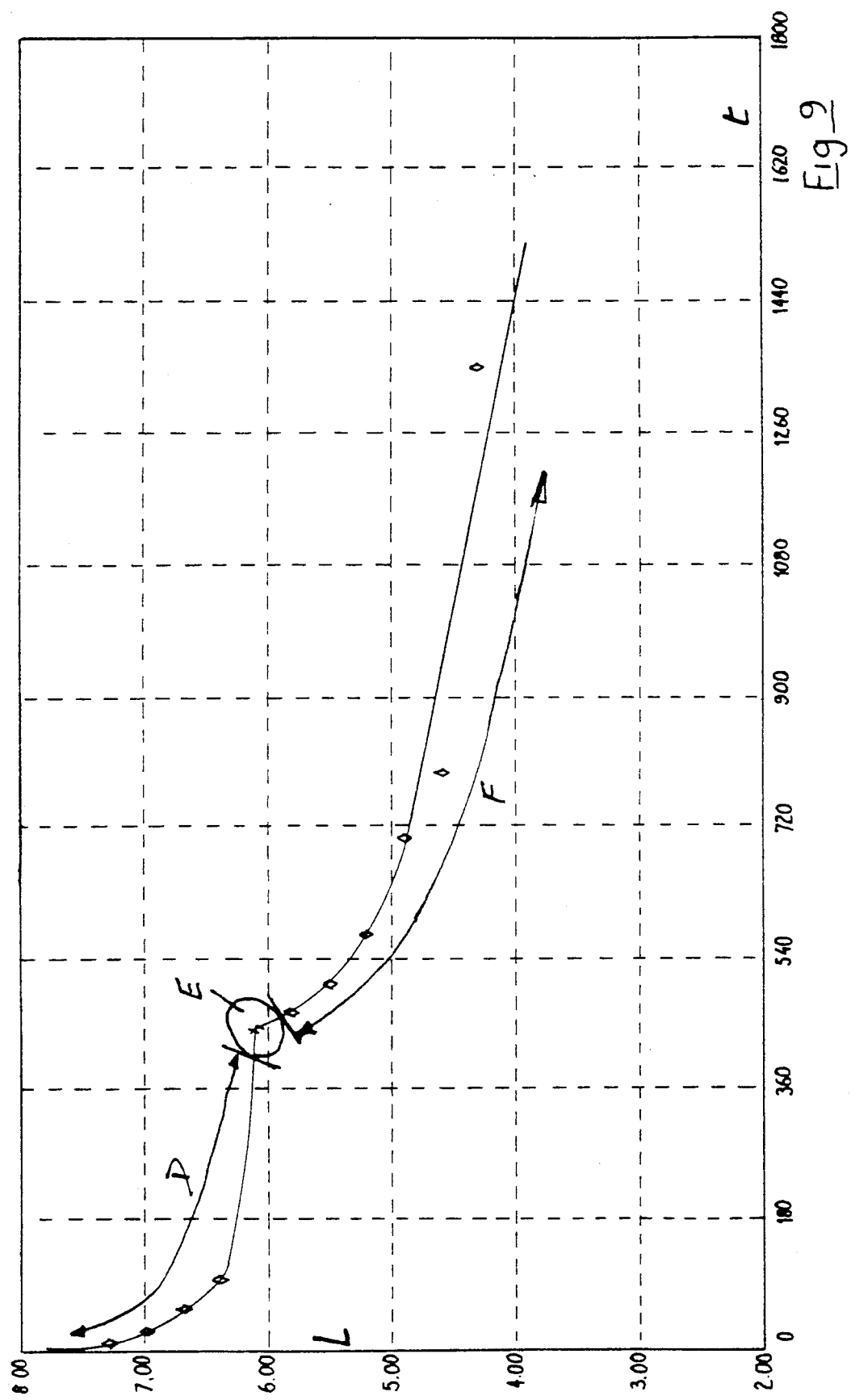

APPARATUS FOR TESTING DARK ADAPTATION

FIELD OF THE INVENTION

The present invention relates to apparatus for testing dark adaptation of the eye of a subject.

BACKGROUND TO THE INVENTION

The process of dark adaptation is the process by which sensitivity of the visual system, namely the eye and the brain to light increases when an individual is placed in darkness. The ability of one or both eyes to adapt to darkness may be impaired by a number of causes, for example nutritional deficiencies, diseases and inherited abnormalities. When the ability of the eye of an individual to adapt to darkness is impaired, either the speed or the extent or both at which the eye can adapt to darkness may be adversely affected. Attempts in the past have been made to provide apparatus for testing dark adaptation of the eye of an individual; however, all such apparatus suffer from disadvantages. In particular, it has been found that such known apparatus are unsatisfactory for use in testing dark adaptation of a child. Further, most tend to be relatively cumbersome and/or relatively expensive and in general most require a relatively skilled operator to measure dark adaptation.

A typical example of apparatus for testing dark adaptation is disclosed in U.S. Pat. No. 3,936,162. This apparatus comprises a face mask having an eye piece for fitting on the subject. A pair of test stimuli provided by two light emitting diodes are mounted in the eye piece so that, in use, the light emitting diodes are in alignment with the optical axis of the subject's eyes. A control circuit provided in a remotely mounted cabinet controls the level of luminance of the diodes in a time ordered sequence. The level of light intensity of the diodes sequentially increases from commencement of the test until it reaches a maximum and then is returned to its minimum value and it increases again sequentially in a time ordered sequence to the maximum and so on. On a subject perceiving the light, the subject operates a switch which stops the sequence. The level of luminance of the diodes when it became visible to the subject is displayed. The person carrying out the test manually times the test and on a level of luminance being displayed records the time and level of luminance. The test is continued in this fashion and the ability of the subject to adapt to darkness is determined from the recorded results.

However, this device is particularly unsuitable for use with children, since a child could indicate that the light emitting diodes were visible to it when in fact they weren't. This obviously would give incorrect results. A further problem with this apparatus is that by virtue of the fact that the level of luminance of the diodes continuously alters in a time ordered sequence, the apparatus tends to give relatively inaccurate results, whether in a child or adult subject. Furthermore, by virtue of the fact that the person carrying out the test must determine the time at which the light emitting diodes become visible to the subject an accurate determination of time is relatively difficult to obtain. Additionally, a further problem with this apparatus is that the area of the retina being tested is limited to the central region. This is because the light emitting diodes are located on the optical axis of the eye, and in close proximity to the eye.

Another apparatus for testing dark adaptation as well as other parameters of the eye is described in British Patent Specification No. 2,114,406. This apparatus comprises a cathode ray tube which displays to a subject a fixation point anywhere in the field of the tube screen and a test stimulus which moves on the screen. The brightness of the test stimulus is adjustable over a range of 10,000 to 1. The background brightness of the screen is also adjustable. By moving the test stimulus and altering the brightness and determining the time at which the test stimulus becomes visible the dark adaptation of the eye of the subject may be determined. However, this device also suffers from the serious disadvantage that it is unsuitable for use with a child since the child could indicate that the test stimulus was visible to it when, in fact, it wasn't, thus giving spurious and inaccurate results. Furthermore, a particular disadvantage of this device is that it tends to be relatively complex, difficult to operate and relatively expensive to produce.

There is therefore a need for apparatus for testing dark adaptation of the eye which overcomes the problems of known apparatus. The present invention is directed towards providing such apparatus.

OBJECTS OF THE INVENTION

One object of the invention is to provide apparatus for testing dark adaptation of the eye of a subject which is relatively easy to use and operate. It is a particular object of the invention to provide such apparatus which is suitable for use in testing dark adaptation of children. A further object of the invention is to provide apparatus for testing dark adaptation of the eye of the subject which is relatively inexpensive. A still further object of the invention is to provide such apparatus which has a relatively low power consumption and can be used in relatively primitive locations and is also not cumbersome.

A further object of the invention is to provide a method for determining dark adaptation of the eye of a subject.

SUMMARY OF THE INVENTION

According to the invention, there is provided apparatus for testing dark adaptation of the eye of a subject, the apparatus comprising:
 a plurality of test stimuli,
 switch means for switching on one of the test stimuli,
 input means for permitting the identity of a test stimulus perceived by the subject to be visible to be inputted,
 comparing means for comparing the identified test stimulus with the test stimulus switched on,
 first selecting means responsive to the comparing means for selecting a test stimulus to be switched on, on a correct identification being made.

In one embodiment of the invention, the input means is operable by the subject.

In another embodiment of the invention, the selecting means is a random selecting means.

In a further embodiment of the invention, second selecting means for selecting the level of luminance of the test stimulus to be switched on is provided, the second selecting means being responsive to the comparing means, the second selecting means sequentially reducing the level of luminance at which a test stimulus is switched on each time the comparing means detects a correct identification.

Preferably, the second selecting means reduces the level of luminance in predetermined decrements.

Preferably, timing means are provided for timing the times at which a correct identification is made by the input means from the time the test commences.

Advantageously, the input means comprises a plurality of manually operable switches, the number of switches corresponding to the number of test stimuli, and each test stimulus having an associated switch provided adjacent thereto.

In one embodiment of the invention, a fixation means is provided the test stimuli being arranged in proximity to the fixation means.

In another embodiment of the invention, the test stimuli are arranged around the fixation means, the fixation means being provided by a light source, and means for reducing the level of luminance of the fixation means is provided.

In one embodiment of the invention, each test stimulus comprises a plurality of light emitting diodes arranged in an array.

In a further embodiment of the invention, alerting means is provided to indicate to a subject when a correct identification of the test stimulus has been made.

Preferably, the first selecting means comprises a random number selector.

In a further embodiment of the invention, display means are provided to display the value of the level of luminance at which a test stimulus is illuminated and the time from the commencement of the test until a correct identification of the test stimulus has been made.

In a still further embodiment of the invention, the apparatus comprises means for recording and storing the levels of luminance at which the test stimuli are illuminated against the respective times from the commencement of the test until the respective test stimuli are correctly identified.

Further, the invention provides a method for testing dark adaptation of the eye of a subject, the method comprising the steps of:

(a) presenting a test stimulus to a subject at a first predetermined level of luminance at the commencement of the test, (b) recording the commencement time at which the test stimulus is presented to the subject at the first predetermined level of luminance, (c) recording the level of luminance of the test stimulus and the time from the commencement time to the time at which the test stimulus becomes visible to the subject, (d) on the test stimulus being visible reducing the level of luminance of the test stimulus to a second predetermined level, (e) recording the second level of luminance and the time from the commencement time to the time the test stimulus becomes visible to the subject at the second level of luminance, (f) repeating steps (d) and (e) a plurality of times and each time recording the level of luminance at which the test stimulus is switched on and the time from the commencement time to the time the test stimulus at that level of luminance becomes visible to the subject.

In one embodiment of the invention, the method includes the step of plotting the recorded levels of luminance against the corresponding recorded times to construct a curve of the subject's response.

In another embodiment of the invention, each time the level of luminance of the test stimulus is reduced the test stimulus is selected from one of a plurality of test stimuli.

In another embodiment of the invention, the test stimulus is randomly selected.

In another embodiment of the invention, a fixation means is presented to the subject simultaneously with the test stimulus.

ADVANTAGES OF THE INVENTION

The advantages of the invention are many. One of the most important advantages of the invention is that it is particularly suitable for use in determining dark adaptation of children. By virtue of the fact that the test stimulus to be switched on may be selected from any one of a number of test stimuli the apparatus is less prone to a subject attempting to indicate visibility of a test stimulus when the test stimulus is in fact not visible to him or her. Further, when the test stimulus is randomly selected from the test stimuli the possibility of an attempt to cheat the apparatus is further reduced.

Another advantage of the invention is that the power requirements of the apparatus are relatively low. This is achieved by virtue of the construction of the apparatus and its related circuitry and method of operation of the apparatus. A further advantage of the invention is that the apparatus is relatively cheap and inexpensive to produce, a particularly important advantage of the invention is that it is relatively simple to operate, and in particular by virtue of the method used by the apparatus for obtaining readings of level of luminance of the test stimulus against time from the commencement of the test to the time the stimulus becomes visible the results can readily easily be plotted to form a curve which graphically represents the dark adaptation of a subject's eye. This is a particularly important advantage, and where the apparatus is provided with means for storing data, the apparatus can readily easily be linked up to a curve plotter which will automatically provide a plot of a curve of the subject's ability to adapt to darkness.

A further advantage of the invention is that it provides a relatively effective and efficient method for testing dark adaptation.

These and other objects and advantages of the invention will be readily apparent to those skilled in the art from the following description of some preferred embodiments thereof given by way of example only, with reference to the drawings.

BRIEF DESCRIPTION OF THE DRAWINGS

FIG. 4 is a block diagram of circuitry of the apparatus of FIG. 1, FIG. 6 is a detailed circuit diagram of other circuitry of the apparatus of FIG. 1, FIG. 9 is a graphical representation of a plot of results received from a test carried out on the apparatus of FIG. 1.

DETAILED DESCRIPTION OF THE INVENTION

Figure 1:
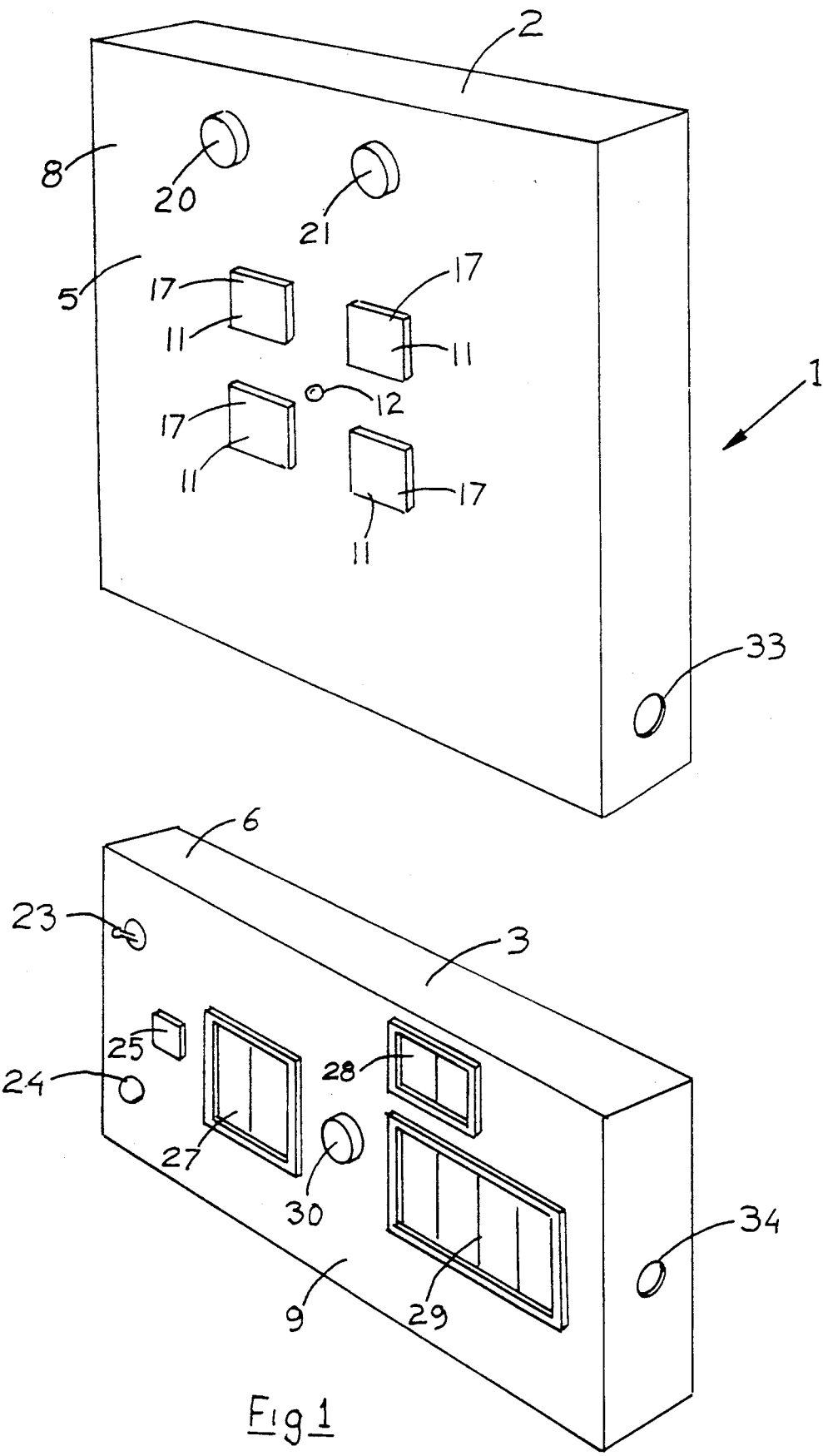
FIG. 1 is a perspective view of apparatus according to the invention for testing dark adaptation of the eye.

Referring to the drawings, there is illustrated apparatus according to the invention indicated generally by the reference numeral 1 for testing dark adaptation of the eye of a subject. The apparatus 1 comprises a test housing 2 and a control housing 3. Both housings 2 and 3 are provided by cabinets 5 and 6 respectively both of which are provided with a front panel, namely a test panel 8 and a control panel 9 respectively. During a test, the test panel 8 is used by the subject as will be described below, and the control 9 is used by the person administering the test.

Figure 2:
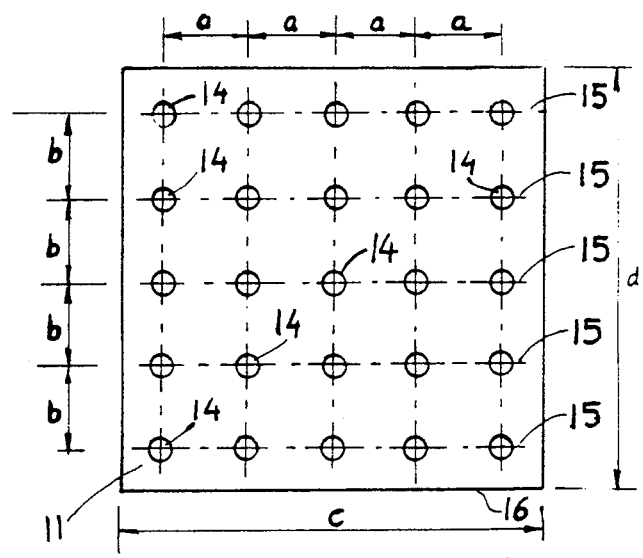
FIG. 2 is an elevational view of a detail of the apparatus of FIG. 1.
Figure 3:
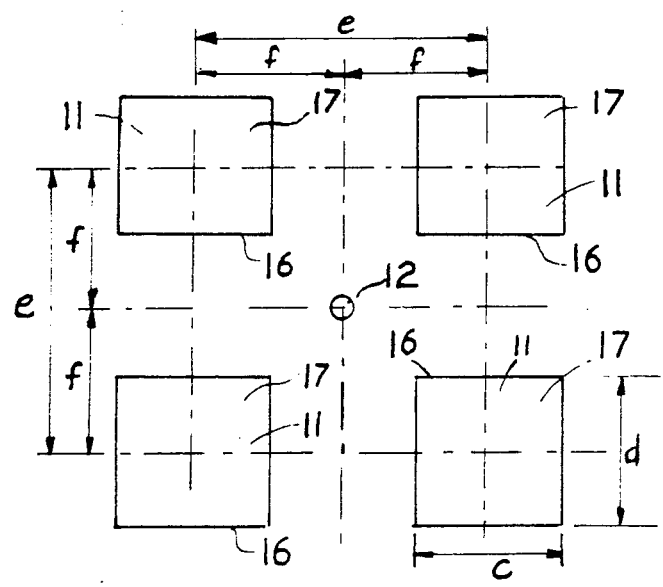
FIG. 3 is an elevational view of a further detail of the apparatus of FIG. 1.

Dealing initially with the test panel 8, a fixation means provided by a red light emitting diode 12 is mounted on the test panel 8 for enabling the subject to focus his or her eyes on the test panel 8 during a test. In this embodiment of the invention, the fixation light emitting diode 12 is of diameter 5 mm. A plurality of test stimuli, namely, four test stimuli 11 are arranged around the fixation light emitting diode 12 on the test panel 8 for testing dark adaptation. Each test stimulus 11 is formed by an array of green light emitting diodes 14, namely five rows 15, each row having five diodes, see FIG. 2. A translucent cover 17 of glass covers the emitting diodes 14 are of diameter 5 mm. Each diode 14 is spaced from its adjacent diodes in each row 15 a distance a, in this case 7 mm centre line to centre line, see FIG. 2. Each row 15 of diodes 14 is spaced from its adjacent rows a distance b, in this case 7 mm centre line to centre line. Each cover 17 comprises a translucent illuminated area 16, namely, c by d, in this case, 35 mm by 35 mm, respectively, for diffusing light from the diodes 14. The light emitting diodes 14 are centrally arranged relative to the area 16. The covers 17 are equi-spaced from and around the fixation light emitting diode 12. The horizontal and vertical distances between the centre lines of the covers 17, namely the dimension e, is 69 mm, see FIG. 3. The horizontal and vertical distances between the centre line of the fixation light emitting diode 12 and the centre line of the covers 17, namely the dimension f, is 34.5 mm.

The fixation light emitting diode 12 remains on throughout a test, however, at any one time, only one test stimulus 11 is switched on. Electronic control circuitry described in detail below comprises switch means for switching on a test stimulus 11 and first selecting means for randomly selecting the test stimulus 11 to be switched on. Second selecting means also provided in the control circuitry selects the level of luminance at which the test stimulus is to be switched on. The fixation light emitting diode 12 and the test stimuli light emitting diodes 14 are so chosen that the wavelength of the light being emitted by the test stimuli 11 is predominantly shorter than the wavelength of the light being emitted by the fixation light emitting diode 12. In this case, the peak wavelength of the fixation light emitting diode 12 is 635 nm (red light), while the wavelength of the test stimuli 11 is 565 nm (green light). This ensures that the appropriate receptors within the retina of the subject's eyes are stimulated. The fixation light emitting diode 12 stimulates the cones preferentially, the test stimuli 11 stimulate the rods.

Figure 5:
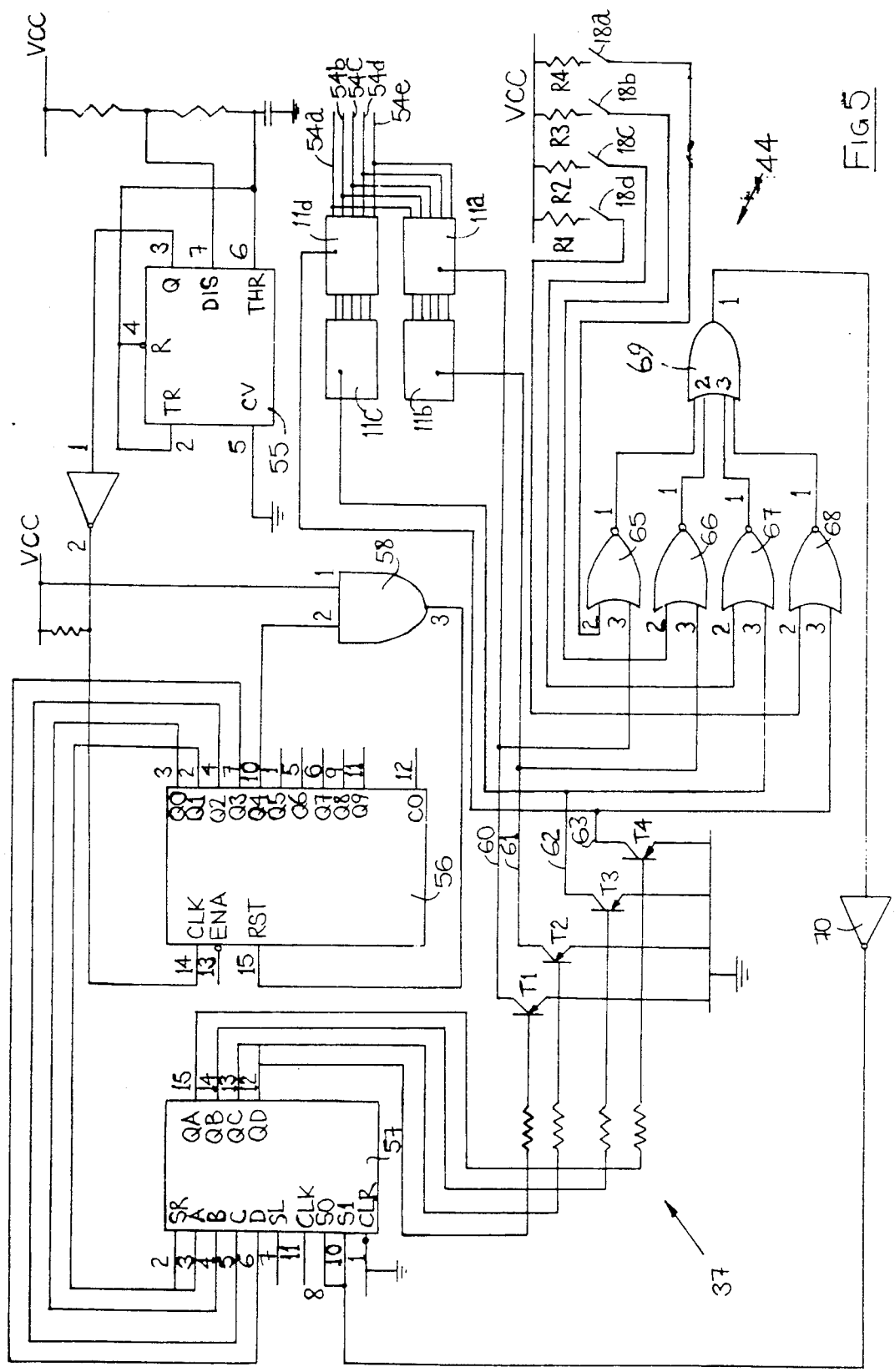
FIG. 5 is a detailed circuit diagram of portion of the apparatus of FIG. 1.

Input means for permitting the subject to input the identity of the test stimulus 11 which is perceived by the subject to be visible is provided by four switches 18 see FIG. 5. Each switch 18 corresponds to a test stimulus 11. Each switch 18 is button operated, and the button of a switch 18 corresponding to a test stimulus 11 is provided adjacent the test stimulus 11, in this case the cover 17 of each test stimulus 11 forms part of the button of the corresponding switch 18. The switches 18, while illustrated in the circuit diagram of FIG. 5, are not illustrated in FIGS. 1 to 3 of the drawings, however, the switches 18 are mounted behind the test panel 8 in the test cabinet 5 in a suitable location. Thus, on a subject perceiving a test stimulus 11 being visible, the subject presses the cover 17 of that test stimulus 11 to operate the switch 18, thus identifying the test stimulus 11 which is perceived to be visible.

During the test, as will be described below, each time a subject correctly identifies a test stimulus 11 as being switched on, the first selecting means randomly selects the next test stimulus 11 to be switched on, and the second selecting means reduces the level of luminance at which the next stimulus 11 is to be switched on by a predetermined decrement.

A pair of alerting means, namely a bell 20 and a buzzer 21 are provided on the test panel 8 to indicate to a subject if the test stimulus 11 is correctly identified. The bell 20 indicates that the correct stimulus has been identified while the buzzer 21 indicates to the subject that an incorrect test stimulus 11 has been identified.

The control housing 3 comprises an on/off mains switch 23 for switching the apparatus 1 on and off mounted on the control panel 9. An indicator lamp 24 on the control panel 9 indicates whether the apparatus 1 is on or off. A start/reset push button 25 is provided on the control panel 9 for activating the apparatus 1 to carry out a test or for resetting the apparatus 1. Display means in this case provided by digital displays 27, 28 and 29 are provided for displaying data and information on a test as the test progresses. The digital display 27 indicates which of the test stimuli 11 are switched on. The digital display 28 displays the level of luminance at which the test stimulus 11 is switched on. The digital display 29 displays time. A two position switch 30 mounted on the control panel 9 selects which time is to be displayed on the digital display 29. In one position of the switch 30, the digital display 29 displays the cumulative time from the time the test commences while in the second position of the switch 30, the digital display 29 displays the time for which a particular test stimulus 11 has been switched on. On a test stimulus 11 being correctly identified as being switched on, the display 29, depending on the position of the switch 30, displays the cumulative time from the commencement of the test to the time the test stimulus was correctly identified or the time that the specific test stimulus 11 was switched on at the particular level of luminance until it was correctly identified.

Cable outlets 33 and 34 are provided in the cabinets 5 and 6 respectively for accommodating a cable connecting the circuitry of both cabinets. In practice, it is envisaged that during a test the cabinets 5 and 6 will be mounted remotely of each other. They may be mounted in the same room, or indeed in certain cases in different rooms. It is believed to be important that the two cabinets should be arranged so that the control panel 9 is not visible to a subject during a test.

Referring now to FIG. 4 a block diagram of the circuitry of the apparatus 1 is illustrated. For convenience, the parts of the circuitry mounted in the respective test and control housings 2 and 3 are grouped together, and the broken lines represent the test and control housings 2 and 3. Thus the components of the circuitry illustrated within the broken lines representing the test housing 2 are mounted within the test housing 2, while the remaining components are mounted within the control housing 3. The switch means and the first selecting means for selecting and switching on a test stimulus 11 is provided in a test stimulus selector circuit 37 which comprises a random number generator as will be described below, and on being activated randomly selects one of the test stimuli 11 to be switched on. The second selecting means for selecting the level of luminance at which the test stimulus 11 is to be switched on is provided by a luminance level control circuit 38 also described below. The level control circuit 38 also controls the luminance level of the fixation light emitting diode 12. In this embodiment of the invention, the level of luminance of the fixation light emitting diode 12 is reduced once on every fourth reduction of the level of luminance of the test stimuli 11. Timing means provided by a clock circuit 39 controls the timing of the apparatus 1. The clock circuit 39 also times a test from the commencement of the test and additionally times the time each individual test stimulus 11 is switched on. A reset circuit 40 which is activated by the start/reset switch 25 and also by the input switches 18 controls the test stimulus selector circuit 37 and the level control circuit 38 through the clock circuit 39. A time display circuit 41, a luminance level display circuit 42 and a stimulus number display circuit 43 drive the digital displays 27, 28 and 29 respectively.

A subject response circuit 44 described in detail below is responsive to the switches 18 and comprises comparing means for comparing the switch 18 operated by the subject with the test stimulus 11 which is switched on. On a correct switch 18 being operated, in other words, on a test stimulus 11 being correctly identified by a subject as being switched on, a bell circuit 45 which drives the alerting bell 20 is activated. A signal is sent through the reset circuit 40 to the clock circuit 39 to record the time at which the correct switch 18 was operated. The clock circuit 39 delivers a signal to the test stimulus selector circuit 37 and the light level selector circuit 38 to select and switch on the next test stimulus 11 and to select the level of luminance of the next test stimulus 11. On the subject response circuit 44 detecting operation of an incorrect switch 18 a buzzer circuit 46 which drives the alerting buzzer 21 is operated to activate the buzzer 21 and to retain the status of the test stimulus 11 unchanged.

Figure 7:
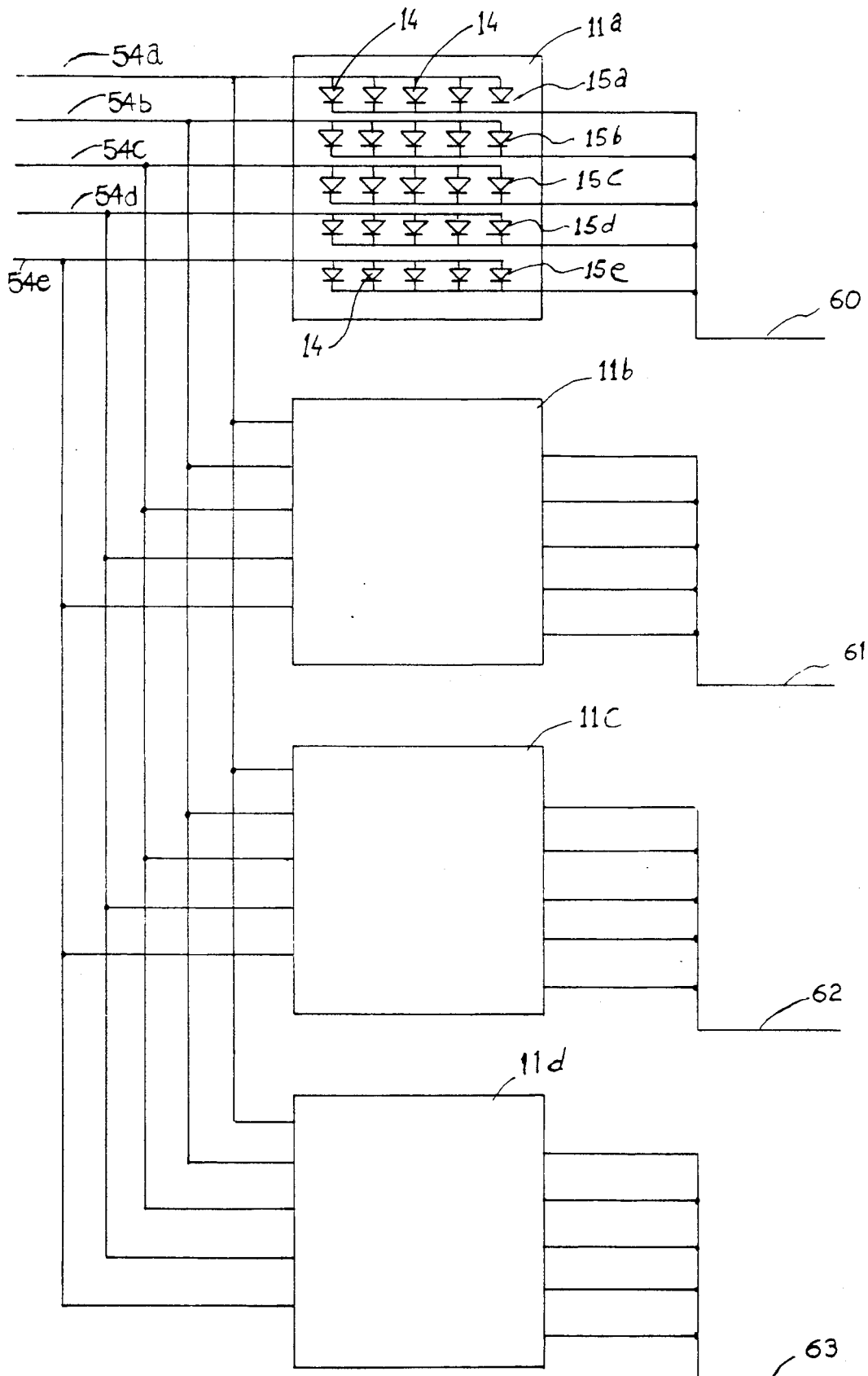
FIG. 7 is a detailed circuit diagram of further circuitry of the apparatus of FIG. 1, FIG. 8(a) to (c) are graphical representations of wave forms used in the operation of the apparatus of FIG. 1.

Referring now to FIGS. 5, 6 and 7 the electronic control circuitry which controls the apparatus 1 will now be described. FIG. 5 illustrates the test stimulus selector circuit 37 and the subject response circuit 44, while FIGS. 6 and 7 illustrate the luminance level control circuit 38. The circuitry of FIGS. 5, 6 and 7 is powered by a power supply circuit indicated generally by the reference numeral 50 and illustrated in FIG. 6. Such power supplies will be well known to those skilled in the art and it is not intended to describe it in further detail here. The power supply circuit 50 receives an input voltage VS of 9 volts on the line 51. A controlled output voltage VCC is provided on an output line 52 of the power supply circuit 50. In this case, the controlled voltage VCC is five volts. One side of the light emitting diodes 14 of the test stimuli 11 are fed from outputs 54 a to e of the luminance level control circuit 38 illustrated in FIG. 6 which will be described in detail below. The outputs 54 a to e applies a high to the diodes 14 to be switched on. The other side of the diodes 14 of the test stimuli 11 are controlled by the selector circuit 37. Returning now to FIG. 5, where the diodes 14 of a test stimulus 11 are to be switched on, a low is applied to the other side of the diodes 14 on an appropriate line 60 to 63 through the switch means which comprises transistors T1 to T4, one transistor T1 to T4 being provided for a corresponding test stimulus 11. The appropriate transistor T1 to T4 is selected by the first selector means for selecting the test stimulus to be switched on. The first selector means comprises a random number generator which comprises a clock chip 55 operating at 100 KHz, a flip-flop counter chip 56 and a one-in-four selector chip 57. The flip-flop counter chip in this case is provided by a 4017 CMOS chip. The chip 56 comprises a divide by ten decade counter with ten decoded outputs. The counter is cleared to a zero count by a logic one on its reset pin 15. The clock chip 55 clocks the counter chip 56 at 100 KHz. An AND gate 58 connected to the fourth output pin, namely pin 10 of the counter chip 56 limits the count sequence of the chip 56. The logic of the chip 56 is arranged so that on the clock pin 14 going high, the output on pin 3 of the AND gate 53 goes high, thereby resetting the counter to zero. Because the counter chip 56 is clocked at the high rate of 100 KHz, stopping the counter results in a discrete pseudo-random output, which controls the operation of the one-in-four selector chip 57. Accordingly, the outputs appearing on pins 12 to 15 of the one-in-four selector chip 57 are randomly selected. A high on any one of the output pins 12 to 15 switches on a corresponding transistor T1 to T4, thereby applying a low to the diodes 14 of the test stimulus 11 selected through the corresponding line 60 to 63. Comparing means for comparing the inputted response of the subject through the switches 18 with the status of the test stimuli 11 is provided by the comparing means in the subject response circuit 44. The comparing means comprises four NOR gates 65 to 68, see FIG. 5. One input 2 of each NOR gate is connected to a respective output of the switches 18. The second input 3 of the NOR gates 65 to 68 is connected to the lines 60 to 63 from the test stimuli 11. The outputs from the NOR gates 65 to 68 are fed into the inputs of an OR gate 69 the output of which is in turn fed through an inverter 70 to the reset pins 9 and 10 of the one-in-four selector chip 57. The switches 18 are connected to the control voltage VCC through resistors R1 to R4 of 1 kohm. Thus, while any switch 18 is open, a low is placed on the input pin 2 of the corresponding NOR gate 65 to 68. On a switch 18 being closed, the input 2 to the corresponding NOR gate 65 to 68 goes high. The lines 60 to 63 of the test stimuli 11 which are switched off are high, thereby putting a high on the input pins 3 of the corresponding NOR gates 65 to 68. On a test stimulus 11 being switched on, the corresponding line 60 to 63 goes low, thereby placing a low on the input pin 3 of the corresponding NOR gate 65 to 68. For example, where the test stimulus 11a is switched on, the line 60 is low and the remaining lines 61 to 63 are high. In this case, a low is placed on the input pin 3 of the NOR gate 65. While the switches 18 are open, each of the pins 2 of the NOR gates 65 to 68 are low. Thus, in this state, the outputs of the NOR gates 66 to 68 on their respective output pins 1 are low, while the output on the output pin 1 of the NOR gate 65 having two lows on its input pins 2 and 3 is high. This thus holds the output on pin 1 of the OR gate 69 high thus indicating that the switch 18a corresponding to the stimulus 11a has not been closed, in other words, operated. Should any other switch 18a be closed, the outputs on the pins 1 of the NOR gates 66 to 68 will remain low, thus leaving the output of the OR gate 69 unaltered. On the correct switch 18a being closed, the input on pin 2 of the NOR gates 65 goes high, thereby putting a low on the output pin 1 of the NOR gate 65. Thus, in this case since all the inputs to the OR gate 69 are low, the output on pin 1 from the OR gate 69 is also low. This thus indicates that the correct switch 18a has been closed. In this state, the inverter 70 applies a high to the reset pins 9 and 10 of the one-in-four selector chip 57 which causes random selection of the next test stimulus 11, by randomly altering the outputs on the pins 12 to 15 of the one-in-four selector 57.

Referring now to FIGS. 6 and 7 the luminance level selector circuit will now be described. The luminance level selector circuit essentially carries out two functions. Firstly, it controls the switching of the rows 15 of light emitting diodes 14 of the test stimulus 11 which is to be switched on, and secondly it controls the length of time the diodes 14 are left switched on. To conserve power, the rows 15 of light emitting diodes 14 of the test stimulus 11 which is switched on are switched on sequentially at the rate of 1 KHz. The level of luminance at which the test stimulus 11 is switched on is determined by the length of time the light emitting diodes 14 of each row 15 are left switched on during the sequential switching.

The rows of diodes 14 of each test stimulus 11 are connected through the lines 54 a to e and transistors T5 to T9 to the five volt control voltage VCC on the output line 52 of the power supply 50.

Figure 8:
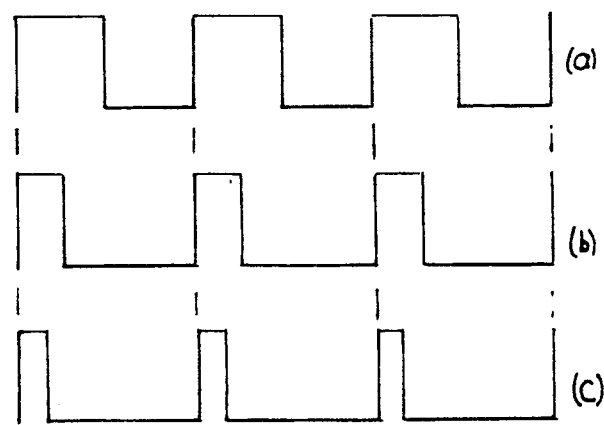

The bases of the transistors T5 to T9 are connected through resistors R5 to R9 of 6.8 kohm to output pins 1 to 5 of a decoder chip 73. The bases of the transistors T5 to T9 are also connected through pull-up resistors R11 to R14 of 1 kohm to the control voltage VCC. Thus, the bases of the transistors T5 to T9 are held high and thus switched off unless a low appears on any of the pins 1 to 5 of the decoder chip 73. The transistors T5 to T9 are selectively switched on by a low being applied sequentially on the pins 1 to 5 of the decoder chip 73. The decoder chip 73 receives binary coded decimal signals on the lines A, B and C from a clock counter chip 74 which cycles at 100 KHz. The decoder chip 73 decodes the signals, and depending on the signal, one of the output pins 1 to 5 of the decoder chip 73 sequentially goes high, thereby switching on the transistors T5 to T7 sequentially. This in turn applies the control voltage VCC through the transistors T5 to T9 sequentially to the rows 15a to e of diodes 14 of the test stimuli 11 through the lines 54 a to e. The time period for which the pins 1 to 5 of the decoder chip 73 remain low is determined by the circuit 76. The circuit 76 applies a square wave signal on the input pin 6 of the decoder chip 73. The length of time a low remains on any of the output pins 1 to 5 of the decoder 73 is determined by the mark space ratio of the square wave signal, see FIG. 8. Maximum luminance is achieved when the mark space ratio is 1:1. Each time the level of luminance is to be reduced, the mark space ratio of the square wave is reduced by the circuit 76. In this embodiment of the invention, the mark space ratio is reduced by a factor of 2 each time the level of luminance is to be reduced. In other words, the time period of the mark is halved each time, see FIG. 7. In this particular embodiment of the invention, the mark can be halved up to sixteen times, this thus gives a range of levels of luminance of 1:64536. In FIG. 7, the mark is illustrated halved three times for the purposes of illustration only.

The signal on the pin 6 of the decoder 73 is derived from an oscillator (not shown) which is modified by the circuit 76. The circuit 76 comprises a timer chip 77 which is used as a retriggerable monostable multivibrator. An output pin 1 of the timer chip 77 is connected to one input pin of an NAND gate 78, the output pin of which is connected to the pin 6 of the decoder chip 73. A signal of the oscillator (not shown) is applied to the other input pin of the NAND gate 78 on a line 85. The signal from the oscillator (not shown) is also applied through the line 85 through the threshold pin 3 of the timer circuit 77. The output on the output pin 1 of the timer chip 77 is controlled by an RC circuit which comprises a capacitor C1 of 100 pF and a digital potentiometer 80 connected in series between the control voltage VCC and ground. The trigger pin 2 of the timer chip 77 is connected between the capacitor C1 and the digital potentiometer 80. A transistor T12 is connected across the capacitor C1. On a low being applied to the base of the transistor T12 by either the threshold pin 3 of the timer pin 77 or the signal on the line 85, the transistor T12 is switched on, thus discharging or preventing the capacitor C1 from charging.

Initially, the capacitor C1 is held discharged by the timer chip 77. At the negative transition of the trigger input pin 2 of the timer chip 77, the capacitor C1 is prevented from charging and is thus discharged through a transistor T12, and the transistor T12 keeps the capacitor C1 discharged until the trigger input pin 2 of the timer chip 77 goes high. The capacitor C1 is then charged. On the voltage across the capacitor C1 reaching two-thirds of the control voltage VCC, the output on the threshold pin 3 of the timer chip 77 goes low and the capacitor C1 is discharged. The transistor T12 continuously discharges the capacitor C1 when the trigger input pin 2 remains low, therefore the output of the timer chip 77 on the threshold pin 3 stays high if the voltage across the capacitor C1 never reaches two-thirds of the voltage VCC. The timer chip 77 outputs a pulse on its output pin 1 which is longer than the input pulse. Thus, the output from the NAND gate 78 effectively decreases the pulse length delivered to pin 6 of the decoder chip 73. In other words, the length of the space of the square wave signal.

An input line 88 to the digital potentiometer 80 receives a high from the inverter 70, see FIG. 5, each time the next test stimulus 11 is to be selected and switched on. The high on the line 88 causes the resistance of the digital potentiometer 80 to change to the next value, to again halve the mark of the mark space ratio of the signal to be applied to pin 6 of the decoder chip 73.

An inverter 81 connected to the output pin 1 of the timer chip 77 is connected to the base of a transistor T14 through a resistor R18 and switches off the control voltage output on the output line 52 from the constant current power supply 50 during the space period of the square wave signal, thereby reducing drain through the resistors R11 to R14.

The clock circuit 39 (not shown in FIGS. 5, 6 or 7 but illustrated in FIG. 4) which controls the operation of the apparatus 1 and also the timer (not shown) which displays the time on the time display 79 is connected to the input pin 2 of the clock counter chip 74 by the line 83. An enable signal is applied to the line 84 of the clock counter chip 74 by the reset circuit 40 on activation of the start/reset switch 25 or on a high being delivered from the inverter 70 on a correct identification of a test stimulus 11 being made by the switches 18. The high on the line 84 is in turn applied to pin 1 of the clock counter chip 74. The reset circuit 25 on activation of the start/reset switch 25 also applies a high to pins 9 and 10 of the one-in-four selector chip 57. The reset circuit 40 is also connected to the input line 88 of the digital potentiometer 80, so that on operation of the start/reset switch 25, the reset circuit 40 resets the resistance value of the digital potentiometer to the value which gives a signal on pin 6 of the decoder 73 with a mark space ratio of 1:1.

Although not illustrated, a suitable control circuit, in this case comprising a chain of resistors (not shown) controls the level of luminance at which the fixation light emitting diode 12 is switched on. This control circuit is connected to the circuit 76, so that on each fourth reduction of the mark space ratio of the signal applied to the pin 6 of the decoder 73, the level of luminance of the fixation light emitting diode 12 is reduced by a predetermined decrement.

A microprocessor (not shown) controls the operation of the apparatus 1. The microprocessor comprises means for storing the times at which the switches 18 correctly identify a test stimulus 11 as being switched on from the commencement time of the test, and the level of luminance at which the test stimulus 11 is switched on. The times are stored against the appropriate level of luminance of the test stimuli. Further, the storing means stores the numbers of the test stimuli which are switched on and their relevant level of luminance. Typical storing means would be provided by a random access memory.

In this embodiment of the invention, the test stimuli are switched on at sixteen different levels of luminance. The levels of luminance are sequentially reduced each time a test stimulus 11 is correctly identified by the subject. The sixteen levels of luminance are set out in Table 1.

TABLE 1

| Test stimulus Sequence | Level of Luminance Test stimuli (micro-micro Lamberts) |
|---|---|
| 1 | $2 \times 10^7$ |
| 2 | $1 \times 10^7$ |
| 3 | $5 \times 10^6$ |
| 4 | $2.5 \times 10^6$ |
| 5 | $1.25 \times 10^6$ |
| 6 | $6.25 \times 10^5$ |
| 7 | $3.125 \times 10^5$ |
| 8 | $1.56 \times 10^5$ |
| 9 | $7.8 \times 10^4$ |
| 10 | $3.9 \times 10^4$ |
| 11 | $1.95 \times 10^4$ |
| 12 | $9.75 \times 10^3$ |
| 13 | $4.875 \times 10^3$ |
| 14 | $2.44 \times 10^3$ |
| 15 | $1.22 \times 10^3$ |
| 16 | $6.1 \times 10^2$ |

In use, with the test housing 2 mounted in a dark room or beneath a hood, the subject to be tested is placed in front of the test housing 2 with the test panel 8 spaced apart from the individuals face a distance of approximately 300 mm. Prior to the test commencing, the subject is exposed to a bright light of fixed duration and luminance in order to bleach the visual pigments of the subject's eyes. The mains on/off power switch 23 is switched on and the start/reset switch 25 is then switched on, thus commencing the test. The fixation light emitting diode 14 is switched on simultaneously with one of the test stimuli 11 which is randomly selected as already described. The test stimulus 11 selected is switched on at maximum luminance, namely, the value corresponding to the first test stimulus of Table 1, namely $2 \times 10^7$ micro-micro Lamberts. At this level of luminance, the mark space ratio of the input of the signal on the input pin 6 of the decoder 73 is 1:1 as illustrated in FIG. 8(a). The timer circuit 39 commences timing from the time the first test stimulus 11 is switched on. The subject focuses on the fixation light emitting diode 12. On the subject perceiving light from a test stimulus to be visible to him or her, the subject presses the cover 17 of the appropriate test light stimulus, thus operating the corresponding switch 18. If the correct switch 18 is activated, the time from commencement of the test to the time the switch 18 is operated is recorded and displayed on the display 29 by appropriately operating the switch 30. The luminance level at which the test stimulus was switched on is also displayed on the display 28. This data is recorded in the microprocessor (not shown). On the correct switch 18 being closed, the next test stimulus 11 is selected by the selector circuit 37 as already described, and the level of luminance at which the next test stimulus 11 is switched on is selected by the level selector circuit 38 as already described. This level of luminance is the level of luminance shown in Table 1 against the test stimulus number 2, namely, $1 \times 10^7$ micro-micro Lamberts. This level of luminance is achieved by halving the time of the mark of the mark space ratio of the signal being applied to the pin 6 of the decoder 73, see FIG. 8(b). The timer circuit 37 continues to time and on the subject correctly identifying the test stimulus 11 which has been switched on, by operating the appropriate switch 18, the time from the commencement of the test to the time at which the switch 18 was operated, and the level of luminance of the test stimulus 11 is recorded and stored in the microprocessor (not shown). This data is also displayed on the displays 28 and 29.

On the correct switch 14 being closed, the next test stimulus 11 is selected and the next reduced level of luminance is also selected by further halving the time of the mark of the signal being applied to pin 6 of the decoder 73. This gives the level of luminance of Table 1 which corresponds with test stimulus number 3. The test continues in this fashion and may be continued until the test stimuli 11 have been switched on at sixteen different levels of luminance. Each time the switched on test stimulus 11 has been correctly identified by the subject, the time from the commencement of the test until correct identification of the test stimulus and the level of luminance of the test stimulus are recorded and stored in the microprocessor.

The microprocessor then can print out the data on time or level of luminance or alternatively can plot a curve of level of luminance against time. At all times during the tests, the fixation light emitting diode 12 remains switched on, however, as the level of luminance of the test stimuli 11 is reduced, the level of luminance of the fixation light emitting diode 12 is also reduced as described above.

On a test stimulus 11 being correctly identified, the alarm 20 is sounded, thereby indicating to the subject that the test stimulus 11 has been correctly identified, so that the subject can then expect the next test stimulus 11. On a test stimulus being incorrectly identified, the buzzer 21 is sounded, thus indicating the fact to the subject. The subject then merely continues to focus on the fixation light emitting diode 12 until light from the switched on stimulus is perceived. Additionally, on an incorrect identification of a test stimulus occurring, the test stimulus 11 remains switched on and the timer continues counting. This state continues until the switched on test stimulus is correctly identified.

A plot of the results, if not made by a printer under the control of the microprocessor of the apparatus 1, is made by the person carrying out the test. A typical plot of the results is illustrated by the curve C in FIG. 9. The level of luminance L is plotted on the y axis, while the time t is plotted on the x axis. The log of the level of luminance L in micro-micro Lamberts is plotted on the Y axis while the time t is plotted in seconds on the x axis. As the level of luminance drops as can be seen the time taken to identify the test stimulus increases. In the curve C the portion D of the curve is referred to as the photopic region. The portion E of the curve C is referred to as the mesopic region. The portion F of the curve C is referred to as the scotopic region. In an average subject with good dark adaptation capabilities, the time distance of the photopic region should be relatively short typically 5 minutes while the time distance of the scotopic region should be of the order of 25 minutes. However, in a subject with poor dark adaptation characteristics the time distance of the photopic region and the scotopic region of the curve C tends to be significantly longer. Thus, by determining the time distance of the photopic and scotopic regions of the curve the ability of a subject's eyes to adapt to darkness can be determined.

While the apparatus has been described as comprising four test stimuli arranged around a fixation light emitting diode, any number of test stimuli may be used without departing from the scope of the invention. Indeed, in certain cases it is envisaged that only two test stimuli may be provided. Further, it will be appreciated that any other arrangement of test stimuli relative to a fixation means may be used without departing from the scope of the invention. It will also be appreciated that the test stimuli may be arranged at other distances from the fixation means than those described. Further, it is envisaged that other suitable test stimuli may be used besides light emitting diodes and besides arrays of light emitting diodes. For example, in certain cases a single light source may be used to form each test stimulus. Where arrays of diodes are used any number of diodes may be used in the array and indeed any arrangement of diodes in the array could be used. Further, it will be appreciated that arrays of other light sources besides light emitting diodes may be used without departing from the scope of the invention. It is also envisaged that while it is advantageous in that considerable power savings are achieved other means for varying the level of luminance of the test stimuli may be used besides that described. Further, other methods for randomly selecting the test stimulus to be switched on from the test stimuli may be used besides that described. It will of course be appreciated that fixation means other than a light emitting diode may be used, and further in all cases it will not be necessary for the level of luminance of the fixation means to be reduced as the level of luminance of the test stimuli is reduced. Indeed, in many cases, the level of luminance of the fixation means may be fixed throughout the test. Additionally, while particular electronic circuitry has been described, other suitable electronic circuitry could be used without departing from the scope of the invention. Needless to say, other means besides NOR and OR gates could be used for comparing the switches 14 with the test stimuli.

In certain cases, the fixation means may be dispensed with altogether.

It is envisaged in certain cases that the apparatus may be provided with only a single housing, in which case the housing would be provided with two panels, one to form the test panel and the other to form the control panel. In many cases, it is envisaged that these panels will be on opposite sides of the housing or on different sides. It is, however, believed to be important that the control panel should not be visible to the subject during the test.

While particular dimensions have been given throughout the specification, it will be readily apparent to those skilled in the art that other dimensions could be used without departing from the scope of the invention.

While the level of luminance of the test stimuli have been reduced by specific decrements on a test stimulus being correctly identified as being switched on, the level of luminance may be reduced by different and/or varying decrements without departing from the scope of the invention.

It will also of course be appreciated that while specific levels of luminance at which the test stimuli are switched on have been given, other levels of luminance may be used without departing from the scope of the invention.

Needless to say, it will be appreciated that while it is preferable that the input means to enable the subject to input the identity of the test stimulus which is perceived to be visible should be provided adjacent the test stimuli, this is not essential. The input means may be remotely provided relative to the test stimuli. Further, it is not essential that the input means be provided by operating buttons of switches within which the test stimuli are provided. Where the input means is to be provided adjacent the test stimuli, the switches may be provided separately on the test panel adjacent the corresponding test stimuli.

It is also envisaged in many cases that a light may be provided on the test panel directed at the subject for the purposes of bleaching the pigments of the subject's eyes. Such a light, it is envisaged, may be independently operated, but preferably would be operated from the control circuitry and on the start/reset switch being depressed to commence a test, it is envisaged that the light would be illuminated for the appropriate duration to bleach the pigments, and on the light being switched off, the test would then commence. At that stage, the timer circuit 37 would commence timing.

While the alerting means for indicating a test stimulus has been correctly identified has been described as being a bell, any other suitable alerting means could be used. For example, in certain cases, it is envisaged that a tune may be played, the use of this or other reinforcement or rewards would be particularly advantageous when the apparatus is being used with children. Similarly, other alerting means besides a buzzer could be used to indicate an incorrect identification of a test stimulus.

In the event of hearing impaired or deaf persons being tested, other suitable means could be provided for alerting the subject to the fact that a correct or incorrect identification has been made. Needless to say, alerting means may also be provided on the control panel for the operator if desired.

It is also envisaged in certain cases that the luminance of the test stimuli may be varied by varying the area of the covers 17 through which light may be transmitted from the diodes or other light source. For example, an iris type diaphragm may be mounted in the covers 17.

While digital displays have been described for indicating information and data, it is envisaged in certain cases that a mimic display consisting of four light emitting diodes indicating which test light source is activated may be provided.

Further, it will be readily apparent to those skilled in the art that the variation of luminance in the various test stimuli and indeed if desired in the fixation means may be achieved by optical or electro-optical or other suitable means.

It is also envisaged in certain cases that where two consecutive incorrect responses are received the apparatus could be arranged to cause reselection of the test stimulus at the current level of luminance.

While the cover of the light emitting diodes of the test stimuli which forms the buttons of the switches 18 have been described as being of glass material it will be appreciated that the covers may be of any other suitable material besides glass, for example, a plastics material or the like. It will of course be appreciated that in certain cases the material may be transparent instead of translucent. It is also envisaged that a neutral density filter could be provided between the light emitting diodes of the test stimuli and the cover, or alternatively, the neutral density filter may be provided over the cover, should the use of a neutral density filter be desirable.

It is also envisaged in certain cases that the fixation means could be movable. For example, a single fixation means may be provided which would be movable over the test panel, or alternatively, a plurality of fixation means may be provided one of which would be switched on at any given time. This would permit testing of different parts of the retina and/or different fields of the retina.

It will also be appreciated that while the first selecting means for selecting the test stimulus to be switched on has been described as being a random selector, any other suitable selecting means for selecting the test stimulus to be switched on may be provided. Indeed, it will be appreciated that in many cases the selection will not be a random selection. Further, it is envisaged that in certain cases the selection of the test stimuli may be arranged in a predetermined fashion to permit testing of different fields of the retina.

While the input means has been described as being provided by a plurality of switches operated by respective buttons, this while it is advantageous is not essential. In many cases, other suitable input means may be used. For example, in certain cases it is envisaged that the input means may be voice sensitive, it may be voice sensitive to the subject or indeed the person operating the apparatus. Further, it will be appreciated that while the input means has been described as being operable by the subject, it could likewise be operable by the operator if desired. Where operable by the operator, it is envisaged that the subject would give some signal to the operator to enable the operator to operate the input means.

It is also envisaged that the test stimuli instead of being in the form of square shapes, could be provided in any other suitable or desirable shape. For example, in certain cases, it is envisaged that the test stimuli could be in the shapes of numbers, letters, animals or the like. In fact, it is envisaged that means to selectively, whether randomly or otherwise, vary the shapes could be provided. Indeed, in certain cases, it is envisaged that each test stimulus may be provided that it may be switched on to form a number of different shapes. This latter embodiment of the invention, it is envisaged, may be of particular benefit in enabling tests to be carried out on a subject when the test has reached the mesopic region of the curve. For example, in such a case, it is envisaged that the test stimuli would be switched on in the shape of squares, and when the test reached the mesopic region, other shapes, for example, letters, numbers or other geometrical shapes could be formed by the test stimuli on being switched on.

While the apparatus has been described for testing dark adaptation of the eyes of a subject, it will be readily apparent to those skilled in the art that it may be used for testing dark adaptation of each individual eye independently of the other.

We claim:

1. Apparatus for testing dark adaptation of the eye of a subject, the apparatus comprising:
   a plurality of test stimuli,
   switch means for switching on any one of the test stimuli,
   input means for permitting the identity of a test stimulus perceived to be visible by the subject to be inputted,
   comparing means for comparing the identified test stimulus with the test stimulus switched on,
   first selecting means responsive to the comparing means for selecting the next test stimulus to be switched on, on a correct identification being made, and
   second selecting means for selecting the level of luminance at which the selected test stimulus is to be switched on, said second selecting means being responsive to the comparing means for selecting the level of luminance of the selected test stimulus at a level less than the level of luminance at which the last correctly identified test stimulus had been switched on.

2. Apparatus as claimed in claim 1 in which the input means is operable by the subject.

3. Apparatus as claimed in claim 1 in which the first selecting means is a random selecting means.

4. Apparatus as claimed in claim 1, in which the second selecting means comprises means for reducing the level of luminance in predetermined decrements.

5. Apparatus as defined in claim 1 further comprising timing means for timing the times at which a correct identification is made by the input means from the time the test commences.

6. Apparatus as claimed in claim 1 in which the input means comprises a plurality of manually operable switches, the number of switches corresponding to the number of test stimuli, and each test stimulus having an associated switch provided adjacent thereto.

7. Apparatus as claimed in claim 1 in which each test stimulus comprises a plurality of light emitting diodes arranged in an array.

8. Apparatus as defined in claim 1 further comprising alerting means to indicate to a subject when a correct identification of the test stimulus has been made.

9. Apparatus as claimed in claim 1 in which the first selecting means comprises a random number selector.

10. A method for testing dark adaptation of the eye of a subject, the method comprising the steps of:
   (a) presenting a test stimulus to a subject at a first predetermined level of luminance at the commencement of the test,
   (b) recording the commencement time at which the test stimulus is presented to the subject at the first predetermined level of luminance,
   (c) recording the level of luminance of the test stimulus and the time from the commencement time to the time at which the test stimulus becomes visible to the subject,
   (d) on the test stimulus being visible reducing the level of luminance of the test stimulus to a second predetermined level,
   (e) recording the second level of luminance and the time from the commencement time to the time the test stimulus becomes visible to the subject at the second level of luminance.
   (f) repeating steps (d) and (e) a plurality of times and each time recording the level of luminance at which the test stimulus is switched on and the time from the commencement time to the time the test stimulus at that level of luminance becomes visible to the subject.

11. A method as claimed in claim 10 in which the method includes the step of plotting the recorded levels of luminance against the corresponding recorded times to construct a curve of the subject's response.

12. A method as claimed in claim 10 in which each time the level of luminance of the test stimulus is reduced, the test stimulus is selected from one of a plurality of test stimuli.

13. A method as claimed in claim 12 in which the test stimulus is randomly selected.

14. A method as claimed in claim 10 in which a fixation means is presented to the subject simultaneously with the test stimulus.

15. Apparatus for testing dark adaptation of the eye of a subject, the apparatus comprising:
   a fixation means,
   a plurality of test stimuli arranged around the fixation means,
   switch means for switching on any one of the test stimuli,
   input means for permitting the identity of a test stimulus perceived to be visible by the subject to be inputted,
   first selecting means responsive to the comparing means for selecting a test stimulus to be switched on, on a correct identification being made,
   second selecting means for selecting the level of luminance of the test stimulus to be switched on, said second selecting means being responsive to the comparing means and comprising means for sequentially reducing the level of luminance at which a test stimulus is switched on each time the comparing means detects a correct identification, and
   means for reducing the level of luminance of the fixation means.

16. Apparatus for testing dark adaptation of the eye of a subject, the apparatus comprising:
   a plurality of test stimuli,
   switch means for switching on any one of the test stimuli.
   input means for permitting the identity of a test stimulus perceived to be visible by the subject to be inputted,
   comparing means for comparing the identified test stimulus with the test stimulus switched on,
   first selecting means responsive to the comparing means for selecting a test stimulus to be switched on, on a correct identification being made,
   second selecting means for selecting the level of luminance of the test stimulus to be switched on, said second selecting means being responsive to the comparing means and comprising means for sequentially reducing the level of luminance at which a test stimulus is switched on each time the comparing means detects a correct identification, and
   display means for displaying the value of the level of luminance at which a test stimulus is illuminated and the time from the commencement of the test until a correct identification of the test stimulus has been made.

17. Apparatus for testing dark adaptation of the eye of a subject, the apparatus comprising:
   a plurality of test stimuli,
   switch means for switching on any one of the test stimuli,
   input means for permitting the identity of a test stimulus perceived to be visible by the subject to be inputted,
   comparing means for comparing the identified test stimulus with the test stimulus switched on.
   first selecting means responsive to the comparing means for selecting a test stimulus to be switched on, on a correct identification being made.
   second selecting means for selecting the level of luminance of the test stimulus to be switched on, said second selecting means being responsive to the comparing means and comprising means for sequentially reducing the level of luminance at which a test stimulus is switched on each time the comparing means detects a correct identification, and
   means for recording and storing the levels of luminance at which the test stimuli are illuminated against the respective times from the commencement of the test until the respective test stimuli are correctly identified.

18. A method for testing dark adaptation of the eye of a subject, the method comprising the steps of:
   presenting a test stimulus of a plurality of test stimuli to a subject,
   permitting the subject to identify the test stimulus perceived to be visible by the subject,
   comparing the identified test stimulus with the test stimulus presented to the subject,
   on a correct identification being made selecting and presenting a test stimulus of the test stimuli to the subject and reducing the level of luminance at which the selected test stimulus is presented to the subject to a level of luminance less than the level of luminance of the last presented test stimulus.

19. A method as claimed in claim 18 in which the method comprises the step of randomly selecting the test stimulus to be presented to the subject.

20. A method as claimed in claim 18 in which the level of luminance at which the test stimuli are to be presented to the subject is reduced in predetermined decrements between each test stimulus being presented to the subject.

* * * * *